US008753617B2

(12) United States Patent
Jager Lezer et al.

(10) Patent No.: US 8,753,617 B2
(45) Date of Patent: Jun. 17, 2014

(54) COMPOSITION IN THE FORM OF A FOAM FOR COATING THE EYELASHES

(75) Inventors: Nathalie Jager Lezer, Verrieres-le-Buisson (FR); Stéphane Arditty, Ballainvilliers (FR); Laure Thiebaut, Clichy (FR)

(73) Assignee: L'Oréal, Paris (FR)

( * ) Notice: Subject to any disclaimer, the term of this patent is extended or adjusted under 35 U.S.C. 154(b) by 1470 days.

(21) Appl. No.: 11/594,965

(22) Filed: Nov. 9, 2006

(65) Prior Publication Data

US 2007/0148114 A1 Jun. 28, 2007

Related U.S. Application Data

(60) Provisional application No. 60/737,389, filed on Nov. 17, 2005.

(30) Foreign Application Priority Data

Nov. 9, 2005 (FR) ........................................ 05 53406

(51) Int. Cl.
*A61Q 1/10* (2006.01)

(52) U.S. Cl.
USPC ........................................................ 424/70.7

(58) Field of Classification Search
None
See application file for complete search history.

(56) References Cited

U.S. PATENT DOCUMENTS

| 2,007,245 | A | 7/1935 | Gimonet |
| 3,937,811 | A | 2/1976 | Papantoniou et al. |
| RE29,871 | E | 12/1978 | Papantoniou et al. |
| 5,162,410 | A | 11/1992 | Sweet |
| 5,866,149 | A * | 2/1999 | Piot et al. ........................ 424/401 |
| 5,874,069 | A | 2/1999 | Mendolia et al. |
| 5,919,441 | A | 7/1999 | Mendolia et al. |
| 5,981,680 | A | 11/1999 | Petroff et al. |
| 6,051,216 | A | 4/2000 | Barr et al. |
| 6,506,372 | B1 * | 1/2003 | Dubief et al. ............... 424/70.13 |
| 6,649,173 | B1 | 11/2003 | Arnaud et al. |
| 6,835,399 | B2 * | 12/2004 | Collin ........................... 424/707 |
| 6,946,518 | B2 * | 9/2005 | De La Poterie ................ 525/50 |
| 7,837,984 | B2 * | 11/2010 | McNamara .................. 424/70.7 |
| 2004/0120920 | A1 | 6/2004 | Lion et al. |
| 2004/0146473 | A1 | 7/2004 | Lion |
| 2004/0235831 | A1 * | 11/2004 | Rozot et al. ................. 514/227.5 |
| 2005/0172421 | A1 | 8/2005 | Jager-Lezer et al. |
| 2005/0191258 | A1 * | 9/2005 | De La Poterie et al. ..... 424/70.1 |
| 2006/0104936 | A1 | 5/2006 | Pays et al. |
| 2006/0115444 | A1 | 6/2006 | Blin et al. |
| 2006/0127341 | A1 | 6/2006 | Lion et al. |
| 2006/0134034 | A1 | 6/2006 | Blin et al. |
| 2006/0134051 | A1 | 6/2006 | Blin et al. |

FOREIGN PATENT DOCUMENTS

| EP | 0 847 752 A1 | 6/1998 |
| EP | 1 396 259 A2 | 3/2004 |
| EP | 1 407 755 A1 | 4/2004 |
| EP | 1 411 069 A2 | 4/2004 |
| FR | 2 232 303 | 1/1975 |
| FR | 2 792 190 A1 | 10/2000 |
| FR | 2824267 | * 11/2002 |
| FR | 2 833 163 A1 | 6/2003 |
| FR | 2844185 | * 3/2004 |
| JP | 2003-286136 | 10/2003 |
| WO | WO 02/47630 | * 6/2002 |
| WO | WO 2004/028488 A2 | 4/2004 |
| WO | WO 2004/055081 A2 | 7/2004 |
| WO | WO 2004/060292 A2 | 7/2004 |
| WO | WO 2004/073626 A2 | 9/2004 |

OTHER PUBLICATIONS

French Search Report for FR 0553406, dated Oct. 11, 2006.
Kirk-Othmer, "Encyclopedia of chemical Technology", Third Edition, vol. 22, John Wiley & Sons, pp. 332-432 (1983).
H.C. Van de Hulst, "Light Scattering by Small Particles," Chapters 9 and 10, John Wiley & Sons, Inc. (1957).
William C. Griffin, "Calculation of HLB Values of Non-ionic Surfactants," The Journal of the Society of Cosmetic Chemists, vol. V, No. 4, pp. 249-256 (1954).
English language abstract of FR 2 792 190 A1, Oct. 20, 2000.
English language abstract of FR 2 833 163 A1, Jun. 13, 2003.
Office Action issued Mar. 13, 2012 in Japan Application No. 2006-303289 (With English Translation).
Office Action issued Jul. 3, 2012 in JP Patent Application No: 2006-303289 (English Translation).

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

Disclosed herein is a process for coating the eyelashes, comprising applying to the eyelashes at least one layer of at least one composition in the form of a foam. Also disclosed herein is a kit for making up and/or for the nontherapeutic care of the eyelashes comprising:
  a container comprising a composition in the form of a foam having a density of less than or equal to 0.95 g/cm$^3$; and
  an applicator comprising at least one application component configured to apply the composition to the eyelashes.

17 Claims, 2 Drawing Sheets

COMPOSITION IN THE FORM OF A FOAM FOR COATING THE EYELASHES

This application claims benefit of U.S. Provisional Application No. 60/737,389, filed Nov. 17, 2005, the contents of which are incorporated herein by reference. This application also claims benefit of priority under 35 U.S.C. §119 to French Patent Application No. FR 05 53406, filed Nov. 9, 2005, the contents of which are also incorporated herein by reference.

Disclosed herein is a process for coating the eyelashes comprising applying, to the eyelashes, a composition in the form of a foam.

The composition may be provided in a form chosen from mascaras and products for the eyebrows.

In at least one embodiment, the composition may be in the form of a mascara.

As used herein, the term "mascara" is understood to mean a composition intended to be applied to the eyelashes: it may be chosen from compositions for making up the eyelashes, bases for making up the eyelashes (also known as base coats), compositions to be applied to a mascara (also referred to as top coats), and compositions for the cosmetic treatment of the eyelashes. The mascara may be applied to the eyelashes of human beings as well as false eyelashes.

Generally, compositions for making up the eyelashes or mascaras may comprise at least one wax or a mixture of waxes dispersed in at least one phase chosen from organic solvents and aqueous liquid phases. They generally exhibit a pasty texture and are packaged in a container comprising a reservoir equipped with a wringer and with an applicator chosen, for example, from brushes and combs, and may be applied by withdrawing the product from the reservoir using the applicator, passing the applicator through the wringer in order to remove the surplus product and then bringing the applicator, impregnated with mascara, into contact with the eyelashes.

Mascaras in the solid form, also referred to as "cake mascaras", which are compositions comprising a high proportion of waxes, pigments, and surfactants and which can be disintegrated with water, that is to say that, prior to being applied to the eyelashes, they have to be brought into contact with an aqueous phase so as to partially dissolve the mascara cake, are described, for example, in U.S. Pat. No. 2,007,245 and French Patent No. 2 833 163. For instance, the application may take place via a brush impregnated with water, which is brought into contact with the mascara, and then the withdrawn mixture may be subsequently applied to the eyelashes with the brush so as to deposit material on the eyelashes.

Disclosed herein is another formulation route for a composition for coating the eyelashes which exhibits a foam texture.

As used herein, the term "composition in the form of a foam" is understood to mean a composition comprising a gas phase (for example, air) in the form of bubbles.

The composition in the form of a foam may exhibit a light texture and may be easy to withdraw and to spread over the eyelashes. It may make it possible, for instance, to obtain a makeup effect, referred to as "starry eyelashes", by the formation of crests in the fringe of eyelashes due to the agglomeration of groups of eyelashes with one another at their upper ends.

The process for coating the eyelashes according to one embodiment of the present disclosure comprises applying the composition to the eyelashes in the form of a foam. This process may be distinguished from the process of the prior art in that the foam is not formed in situ on the eyelashes, that is to say that the foam is not created after application of the composition. In at least one embodiment, it is not a delayed expansion composition, which is a system in which a "volatile" agent is released or formed in the composition after the latter has been applied to the eyelashes. As used herein, the term "delayed-expansion compositions" are compositions created after exposure of a gel to atmospheric pressure and/or to shearing and/or to a temperature greater than ambient temperature.

Disclosed herein is a process for coating the eyelashes comprising applying to the eyelashes at least one layer of at least one composition in the form of a foam, wherein the composition has a density of less than or equal to 0.95 g/cm$^3$ and a plate rigidity modulus Gp of less than 50 000 Pa.

Also disclosed herein is a process for coating the eyelashes comprising applying to the eyelashes at least one layer of at least one composition in the form of a foam form, wherein the composition has a density of less than or equal to 0.95 g/cm$^3$ and a dry matter content of less than or equal to 60% by weight, with respect to the total weight of the composition.

According to one embodiment, the composition may comprise a liquid fatty phase and a fatty-phase structuring agent. Another embodiment of the present disclosure is directed to a process for coating the eyelashes comprising applying to the eyelashes at least one layer of at least one composition in the form of a foam, wherein the composition has a density of less than or equal to 0.95 g/cm$^3$ and comprises at least one liquid fatty phase and at least one fatty-phase structuring agent.

According to another embodiment, the composition may comprise at least one aqueous phase and at least one hydrophilic gelling agent. Yet another embodiment of the present disclosure is directed to a process for coating the eyelashes comprising applying to the eyelashes at least one layer of at least one composition in the form of a foam, wherein the composition has a density of less than or equal to 0.95 g/cm$^3$ and comprises at least one aqueous phase and at least one hydrophilic gelling agent.

Also disclosed herein is a kit for making up and/or for the nontherapeutic care of the eyelashes comprising:

a composition in the form of a foam having a density of less than or equal to 0.95 g/cm$^3$ and an applicator comprising at least one application component configured in order to apply the composition to the eyelashes.

MEASUREMENT PROTOCOLS

Density

Figure 1:
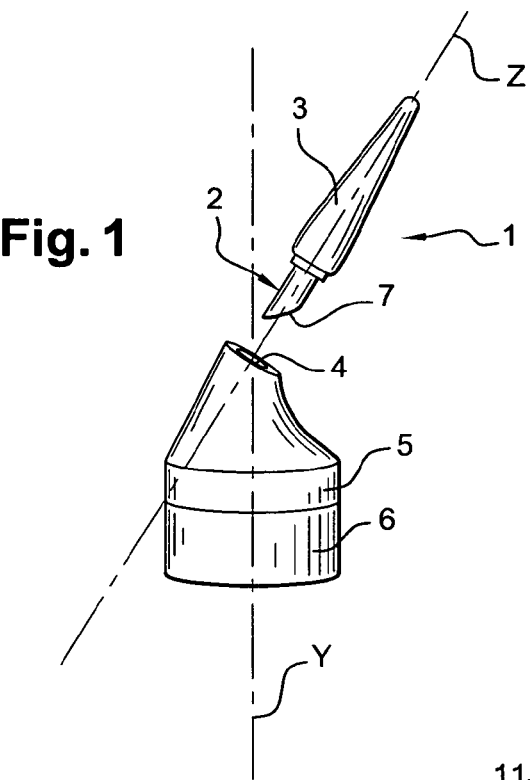
FIG. 1 illustrates a first embodiment of an applicator suitable for use in the kits of the present disclosure.

The density is measured according to the following protocol: a container, the volume Vo (cm$^3$) of which is known with an accuracy of ±0.005 cm$^3$ (Vo being of the order of 10 cm$^3$), is weighed by means of a precision balance to ±0.00005 g. Its weight is recorded as Wo (g). This container is carefully filled with the foam until the container overflows. The surface of the container is then levelled with a straight blade in order to obtain a perfectly flat foam surface. The weight W (g) of the container filled with foam is then measured.

The density corresponds to the ratio of the density of the composition, calculated as follows:

$$\rho_v \text{ (g/cm}^3\text{)} = \frac{W - Wo}{Vo}$$

to the density of water (1 g/cm$^3$).

In at least one embodiment, the composition employed in the process according to the present disclosure has a density of less than or equal to 0.95 g/cm$^3$, for example, less than or equal to 0.9 g/cm$^3$, or less than or equal to 0.8 g/cm$^3$. In another embodiment, the density of the composition is greater than or equal to 0.1 g/cm$^3$, for instance, greater than or equal to 0.2 g/cm$^3$.

Solids Content

The compositions according to the present disclosure may have a dry matter (or solids content) of less than or equal to 60% by weight, with respect to the total weight of the composition, for example, less than or equal to 55% by weight, or less than or equal to 50% by weight, with respect to the total weight of the composition.

In at least one embodiment, the solids content may be greater than or equal to 10% by weight, for instance, ranging from 35 to 50% by weight, with respect to the total weight of the composition.

The dry matter content, that is to say the content of non-volatile matter, may be measured in various ways, for example, by drying in an oven, by drying by exposure to infrared radiation, and by assaying the water according to the Karl Fischer technique.

According to one embodiment, the dry matter content, commonly referred to as "solids content", of the compositions according to the present disclosure may be measured by heating the sample by infrared rays with a wavelength of 2 μm to 3.5 μm. The substances present in the compositions which have a high vapor pressure evaporate under the effect of this radiation. The measurement of the loss in weight of the sample makes it possible to determine "the solids content" of the composition. These measurements are carried out by means of a Mettler LP16 commercial infrared dryer. This technique is described, for example, in the documentation of the device supplied by Mettler.

The measurement protocol is as follows:

Approximately 1 g of the composition is spread over a metal dish. The latter, after introduction into the dryer, is subjected to a set temperature of 120° C. for 1 hour. The wet weight of the sample, corresponding to the starting weight, and the dry weight of the sample, corresponding to the weight after exposure to the radiation, are measured by means of a precision balance.

The content of dry matter is calculated according to the following formula:

solids content=100×(dry weight/wet weight).

Rheological Characterizations

According to one embodiment, the compositions in accordance with the present disclosure may have a viscoelastic behavior.

Generally, a material is said to be viscoelastic when, under the effect of shearing, it has both the characteristics of an elastic material, that is to say capable of storing energy, and the characteristics of a viscous material, that is to say capable of dissipating energy.

The viscoelastic behavior of the compositions in accordance with the present disclosure may be characterized, for example, by their rigidity modulus G. This parameter is defined, for instance, in "Initiation à la rhéologie [Introduction to Rheology]", G. Couarraze and J. L. Grosslord, 2nd edition, 1991, published by Lavoisier-Tec 1 Doc.

The measurements are carried out on an RS 600 controlled-stress rheometer from ThermoRheo equipped with a thermostatically-controlled bath and with a stainless steel rotor possessing plate/plate geometry, the plate having a diameter of 20 mm and there being an air gap (distance between the lower plate, referred to as stator plate, on which the composition is deposited, and the upper plate, referred to as rotor plate) of 1 mm. The two plates are striated in order to limit the slipping phenomena at the walls of the plates. Care is taken to charge the foam by approaching the plates at the minimum speed of the device (0.6 mm/min) in order not to destructure the foam during charging to the rheometer. The measurements are carried out at 25° C.±0.5° C.

The dynamic measurements are carried out by applying a harmonic variation in the stress. In these experiments, the amplitudes of the shear stress (recorded as τ) and of the shear strain (recorded as γ) are low so as to remain within the limits of the linear viscoelastic domain of the composition (conditions making it possible to evaluate the rheological characteristics of the composition at rest).

The linear viscoelastic domain is generally defined by the fact that the response of the material (i.e., the strain) is at any time directly proportional to the value of the force applied (i.e., the stress). In this domain, the stresses applied are low and the material is subjected to strains without modifying its microscopic structure. Under these conditions, the material is studied "at rest" and non-destructively.

The composition is subjected to harmonic shearing according to stress τ(t) varying sinusoidally according to a pulsation ω (ω=2π), ν being the frequency of the shearing applied. The composition thus sheared is subjected to a stress τ(t) and responds according to a strain γ(t) corresponding to microdeformations for which the rigidity modulus does not vary very much as a function of the stress applied.

The stress τ(t) and the strain γ(t) are defined respectively by the following relationships:

τ(t)=τ$_0$ cos(ω·t) γ(t)=γ$_0$ cos(ω·t−δ)

τ$_0$ being the maximum amplitude of the stress and γ$_0$ being the maximum amplitude of the strain. The elasticity δ is the angle of phase difference between the stress and the strain.

The measurements are carried out at a frequency of 1 Hz (ν=1 Hz).

Increasing stresses are applied to the sample, starting from an initial stress equal to 3 Pa to arrive at a final stress of 4000 Pa, the stresses only being applied once.

The change in the rigidity modulus G (corresponding to the ratio of τ$_o$ to γ$_0$) and in the elasticity δ (corresponding to the angle of phase difference of the stress applied with respect to the strain measured) as a function of the stress τ(t) applied is thus measured.

In at least one embodiment, the strain of the composition for the stress region in which the variation in the rigidity modulus G and in the elasticity δ is less than 7% (region of microdeformations) is measured and the "plateau" parameter Gp is thus determined.

The viscoelastic behavior of the compositions according to the present disclosure may be characterized, for example, by a plateau rigidity modulus Gp of less than 50 000 Pa, for instance, less than or equal to 25 000 Pa, less than or equal to 15 000 Pa, or less than or equal to 10 000 Pa.

In at least one embodiment, the compositions according to the present disclosure may have a plateau rigidity modulus Gp of greater than or equal to 100 Pa, for example, greater than or equal to 300 Pa.

Size of the Bubbles

The composition according to the present disclosure is in the form of a foam, and thus, comprises gas bubbles, for instance, air bubbles.

In one embodiment of the present disclosure, the air bubbles in the composition may have a number-average diameter of less than or equal to 1 mm, for example, ranging from 0.1 µm to 1 mm, or less than or equal to 0.8 mm.

The number-average diameter is determined in the following way: the foam is packaged in a jar from the end of the preparation, when it is still fluid. The size of the bubbles is observed by taking a digital photograph of the surface of the jar 24 h after manufacture or after opening the packaging after having levelled the surface, then, using "Saisam" imaging processing software, by counting the number of bubbles over the surface area of approximately 1 cm$^2$ and by determining their number-average diameter.

According to one embodiment, the composition employed in the process according to the present disclosure may be a leave-in composition.

Compositions

Fatty Phase

The composition according to the present disclosure may comprise at least one fatty phase, for instance, a liquid fatty phase.

As used herein, the term "liquid fatty phase" is understood to mean a fatty phase which is liquid at ambient temperature (25° C.) and atmospheric pressure (760 mmHg) and which comprises at least one nonaqueous fatty substances, compatible with one another, which may be liquid at ambient temperature, also referred to as oils.

The oil may, for example, be chosen from volatile oils, nonvolatile oils, and mixtures thereof.

The at least one liquid fatty phase may be present in the composition in an amount ranging from 0.1% to 30% by weight, for instance, from 1% to 20% by weight, with respect to the total weight of the composition.

As used herein, the term "volatile oil" is understood to mean an oil capable of evaporating on contact with the skin or with the keratinous fiber in less than one hour at ambient temperature and atmospheric pressure. The at least one volatile organic solvent and the at least one volatile oil of the present disclosure may be volatile cosmetic organic solvents and oils which are liquid at ambient temperature and which have a nonzero vapor pressure, at ambient temperature and atmospheric pressure, ranging, for example, from 0.13 Pa to 40 000 Pa ($10^{-3}$ to 300 mmHg), from 1.3 Pa to 13 000 Pa (0.01 to 100 mmHg), or from 1.3 Pa to 1300 Pa (0.01 to 10 mmHg).

As used herein, the term "nonvolatile oil" is understood to mean an oil which remains on the skin or the keratinous fiber at ambient temperature and atmospheric pressure for at least several hours and which has, for instance, a vapor pressure of less than $10^{-3}$ mmHg (0.13 Pa).

In at least one embodiment, these oils may be chosen from hydrocarbon oils, silicone oils, fluorinated oils, and mixtures thereof.

As used herein, the term "hydrocarbon oil" is understood to mean an oil comprising mainly hydrogen and carbon atoms and optionally at least one atom chosen from oxygen, nitrogen, sulphur, and phosphorus. Volatile hydrocarbon oils may be chosen, for example, from hydrocarbon oils comprising from 8 to 16 carbon atoms, for instance, branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane, and isohexadecane, for example the oils sold under the tradenames Isopar and Permethyl, branched $C_8$-$C_{16}$ esters, isohexyl neopentanoate, and mixtures thereof. Other examples of suitable volatile hydrocarbon oils include, but are not limited to, petroleum distillates, such as those sold under the Shell Solt name by Shell. In at least one embodiment, the volatile solvent may be chosen from volatile hydrocarbon oils comprising from 8 to 16 carbon atoms and mixtures thereof.

Further non-limiting examples of volatile oils include volatile silicones, such as volatile linear and cyclic silicone oils, such as those having a viscosity ≤8 centistokes ($8 \times 10^{-6}$ m$^2$/s) and comprising, for instance, from 2 to 7 silicon atoms, these silicones optionally comprising at least one group chosen from alkyl and alkoxy groups comprising from 1 to 10 carbon atoms. In one embodiment, the at least one volatile silicone oil may be chosen from octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

Other non-limiting examples include the volatile linear alkyltrisiloxane oils of formula (I)

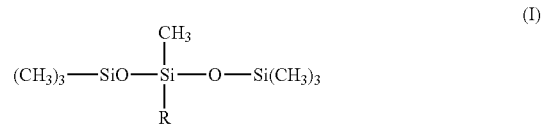

wherein R is chosen from alkyl groups comprising from 2 to 4 carbon atoms, in which optionally at least one hydrogen atom may be substituted by an atom chosen from fluorine and chlorine atoms.

Examples of oils of formula (I) include, but are not limited to:

3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is respectively chosen from butyl groups, propyl groups, and ethyl groups.

The at least one volatile oil may also be chosen from volatile fluorinated solvents, such as nonafluoromethoxybutane and perfluoromethylcyclopentane.

The composition may also comprise at least one nonvolatile oil, chosen, for example, from nonvolatile hydrocarbon oils, nonvolatile silicone oils, and/or nonvolatile fluorinated oils.

Suitable nonvolatile hydrocarbon oils may include, for example:
  hydrocarbon oils of vegetable origin, such as triesters of fatty acids and of glycerol, the fatty acids of which may have varied chain lengths ranging from $C_4$ to $C_{24}$, it being possible for these chains to be linear or branched and saturated or unsaturated; these oils including, but not limited to, wheat germ, sunflower, grape seed, sesame, maize, apricot kernel, castor, shea, avocado, olive, soybean, sweet almond, palm, rapeseed, cottonseed, hazelnut, macadamia, jojoba, alfalfa, poppy, pumpkinseed, cucumber, blackcurrant seed, evening primrose, millet, barley, quinoa, rye, safflower, candlenut, passionflower, and musk rose oils; and triglycerides of caprylic/capric acids, such as those sold by Stearineries Dubois and those sold under the names Miglyol 810, 812, and 818 by Dynamit Nobel, synthetic ethers comprising from 10 to 40 carbon atoms;

linear or branched hydrocarbons of mineral or synthetic origin, such as liquid petrolatum, polydecenes, hydrogenated polyisobutene, such as Parleam oil, squalane, and mixtures thereof;

synthetic esters, such as the oils of formula $R_1COOR_2$, wherein $R_1$ is chosen from residues of linear or branched fatty acids comprising from 1 to 40 carbon atoms and $R_2$ is chosen from hydrocarbon chain, for example, branched hydrocarbon chains, comprising from 1 to 40 carbon atoms, with the proviso that the total number of carbon atoms of $R_1+R_2$ is $\geq 10$, such as Purcellin oil (ketostearyl octanoate), isopropyl myristate, isopropyl palmitate, $C_{12}$ to $C_{15}$ alkyl benzoate, hexyl laurate, diisopropyl adipate, isononyl isononanoate, 2-ethylhexyl palmitate, isostearyl isostearate, octanoates, decanoates, and ricinoleates of alcohols and polyalcohols, such as propylene glycol dioctanoate; hydroxylated esters, such as isostearyl lactate and diisostearyl malate; and pentaerythritol esters;

fatty alcohols comprising a branched and/or unsaturated carbon chain comprising from 12 to 26 carbon atoms which are liquid at ambient temperature, such as octyldodecanol, isostearyl alcohol, oleyl alcohol, 2-hexyldecanol, 2-butyloctanol, and 2-undecylpentadecanol;

higher fatty acids, such as oleic acid, linoleic acid, and linolenic acid;

carbonates;

acetals;

citrates;

and mixtures thereof.

The nonvolatile silicone oils which may be used in the compositions according to the present disclosure may be chosen, for example, from polydimethylsiloxanes (PDMSs) which are nonvolatile, polydimethylsiloxanes comprising at least one group chosen from pendent groups such as alkyl and alkoxy groups and/or groups at the end of the silicone chain, such as alkyl and alkoxy groups, these groups each comprising from 2 to 24 carbon atoms, phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, and (2-phenylethyl)trimethylsiloxysilicates.

The at least one fluorinated oil which may be used in accordance with the present disclosure may be chosen, for instance, from fluorosilicone oils, fluorinated polyethers, and fluorinated silicones, such as those disclosed in European Patent No. 0 847 752.

According to one embodiment, the at least one fatty phase may comprise at least one ester oil, chosen, for example, from the esters of monocarboxylic acids with monoalcohols and polyalcohols.

In another embodiment, the at least one ester may be chosen from those of formula (I):

$$R_1-CO-O-R_2 \quad (I)$$

wherein $R_1$ is chosen from linear or branched alkyl radicals comprising from 1 to 40 carbon atoms, for example, from 7 to 19 carbon atoms, optionally comprising at least one ethylenic double bond, and optionally substituted, $R_2$ is chosen from linear or branched alkyl radicals comprising from 1 to 40 carbon atoms, for example, from 3 to 30 carbon atoms, or from 3 to 20 carbon atoms, optionally comprising at least one ethylenic double bond, and optionally substituted.

As used herein, the term "optionally substituted" is understood to mean that $R_1$ and/or $R_2$ may carry at least one substituent chosen, for example, from groups comprising at least one heteroatom chosen from O, N, and S, such as amino, amine, alkoxy, and hydroxyl.

In one embodiment, the total number of carbon atoms of $R_1+R_2$ is $\geq 9$.

$R_1$ may be chosen from residues of linear or, in at least one embodiment, branched fatty acids, for example, higher fatty acids, comprising from 1 to 40, for instance, from 7 to 19 carbon atoms and $R_2$ may be chosen from linear or, in at least one embodiment, branched hydrocarbon chains comprising from 1 to 40, for instance, from 3 to 30, or from 3 to 20 carbon atoms. According to this embodiment, the total number of carbon atoms of $R_1+R_2$ may be $\geq 9$.

Examples of suitable $R_1$ groups include, but are not limited to, those derived from the fatty acids chosen from acetic, propionic, butyric, caproic, caprylic, pelargonic, capric, undecanoic, lauric, myristic, palmitic, stearic, isostearic, arachidic, behenic, oleic, linolenic, linoleic, eleostearic, arachidonic, and erucic acids, and mixtures thereof.

Non-limiting examples of esters include Purcellin oil (ketostearyl octanoate), isononyl isononanoate, isopropyl myristate, 2-ethylhexyl palmitate, 2-octyldodecyl stearate, 2-octyldodecyl erucate, isostearyl isostearate and the heptanoates, octanoates, decanoates, and ricinoleates of alcohols and polyalcohols, for example of fatty alcohols.

According to one embodiment, the at least one ester may be chosen from the compounds of the above formula (I), wherein $R_1$ is chosen from unsubstituted linear or branched alkyl groups comprising from 1 to 40 carbon atoms, for example, from 7 to 19 carbon atoms, optionally comprising at least one ethylenic double bond and $R_2$ is chosen from unsubstituted linear or branched alkyl groups comprising from 1 to 40 carbon atoms, for example, from 3 to 30 carbon atoms, or from 3 to 20 carbon atoms, optionally comprising at least one ethylenic double bond.

In another embodiment, $R_1$ is chosen from unsubstituted branched alkyl groups comprising from 4 to 14 carbon atoms, for example, from 8 to 10 carbon atoms, and $R_2$ is chosen from unsubstituted branched alkyl groups comprising from 5 to 15 carbon atoms, for example, from 9 to 11 carbon atoms. According to yet another embodiment, in formula (I), $R_1$—CO— and $R_2$ have the same number of carbon atoms and derive from the same radical, such as unsubstituted branched alkyl radicals, for example isononyl, that is to say that, in at least one embodiment, the molecule of ester oil is symmetrical.

The at least one ester oil may be chosen, for instance, from the following compounds:

isononyl isononanoate,
ketostearyl octanoate,
isopropyl myristate,
2-ethylhexyl palmitate,
2-octyldodecyl stearate,
2-octyldodecyl erucate, and
isostearyl isostearate.

Structuring Agent

The composition according to the present disclosure may comprise at least one liquid-fatty-phase structuring agent chosen from pasty fatty substances, semicrystalline polymers, lipophilic gelling agents, and mixtures thereof.

The at least one structuring agent may be present in the composition in an amount ranging from 0.1 to 60% by weight, with respect to the total weight of the composition, for example, from 0.5 to 50% by weight, or from 1 to 40% by weight.

The amount of the at least one oily structuring agent can be adjusted by a person skilled in the art according to the structuring properties of the at least one agent.

Pasty Fatty Substances

As used herein, the term "pasty fatty substance" is understood to mean a lipophilic fatty compound comprising, at a temperature of 23° C., a liquid fraction and a solid fraction.

In at least one embodiment, the pasty compound may have a hardness at 20° C. ranging from 0.001 to 0.5 MPa, for example, from 0.002 to 0.4 MPa.

The hardness is measured according to a method of penetration of a probe into a sample of compound, for instance, using a texture analyser (for example, the TA-XT21 from Rheo) equipped with a stainless steel cylinder with a diameter of 2 mm. The hardness measurement is carried out at 20° C. at the center of 5 samples. The cylinder is introduced into each sample at a pre-rate of 1 mm/s and then at a measuring rate of 0.1 mm/s, the depth of penetration being 0.3 mm. The value recorded for the hardness is that of the maximum peak.

In at least one embodiment, the liquid fraction of the pasty compound measured at 23° C. may range from 9 to 97% by weight of the compound. According to another embodiment, the liquid fraction at 23° C. may range from 15 to 85%, for example, from 40 to 85%, by weight. The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound to change from the solid state to the liquid state. The pasty compound is "in the solid state" when the whole of its mass is in the crystalline solid form. The pasty compound is "in the liquid state" when the whole of its mass is in the liquid form.

The enthalpy of fusion of the pasty compound is equal to the area under the curve of the thermogram obtained using a differential scanning calorimeter (DSC), such as the calorimeter sold under the name MDSC 2920 by TA Instrument, with a rise in temperature of 5 to 10° C. per minute, according to the standard ISO 11357-3:1999. The enthalpy of fusion of the pasty compound is the amount of energy necessary to change the compound from the solid state to the liquid state. It is expressed in J/g.

The enthalpy of fusion consumed at 23° C. is the amount of energy absorbed by the sample to change from the solid state to the state which it exhibits at 23° C., composed of a liquid fraction and of a solid fraction.

According to another embodiment, the liquid fraction of the pasty compound measured at 32° C. may range from 30 to 100% by weight of the compound, for example, from 80 to 100%, or from 90 to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

Suitable pasty substances may include, but are not limited to, hydrocarbon compounds, such as lanolins and their derivatives, and PDMSs.

Semicrystalline Polymers

As used herein, the term "polymer" is understood to mean compounds comprising at least two repeat units, for instance, at least 3 repeat units, or at least 10 repeat units. As used herein, the term "semicrystalline polymer" is understood to mean polymers comprising at least one crystallizable part, at least one crystallizable pendent chain, and/or at least one crystallizable block in the backbone and an amorphous part in the backbone and exhibiting a first-order reversible phase change temperature, for example, a melting point (solid-liquid transition). When the at least one crystallizable part is in the form of a crystallizable block of the polymer backbone, the amorphous part of the polymer is in the form of an amorphous block; the semicrystalline polymer is in this case a block copolymer, for example diblock, triblock, and multiblock copolymers, comprising at least one crystallizable block and at least one amorphous block. As used herein, the term "block" is understood to mean generally at least 5 identical repeat units. The at least one crystallizable block or blocks are then different in chemical nature from the amorphous block or blocks.

A semicrystalline polymer generally has a melting point of greater than or equal to 30° C., for example, ranging from 30° C. to 80° C., or from 30° C. to 60° C. This melting point is a first-order change in state temperature.

This melting point can be measured by any known method, for example, methods using a differential scanning calorimeter (DSC).

In at least one embodiment, the at least one semicrystalline polymer may have a number-average molecular weight $\overline{M}n$ of greater than or equal to 1000, for example, ranging from 2000 to 800 000, from 3000 to 500 000, or from 4000 to 150 000, and in another embodiment, less than 100 000, or from 4000 to 99 000. According to yet another embodiment, the at least one semicrystalline polymer may have a number-average molecular weight of greater than 5600, for example, ranging from 5700 to 99 000. As used herein, the term "crystallizable chain or block" is understood to mean a chain or block which, if it were alone, would change reversibly from the amorphous state to the crystalline state according to whether the temperature is above or below the melting point. As used herein, the term "chain" refers to a group of atoms which is pendent or lateral with respect to the backbone of the polymer. As used herein, a "block" is a group of atoms belonging to the backbone, and comprising at least one of the repeat units of the polymer. In at least one embodiment, the "crystallizable pendent chain" may be a chain comprising at least 6 carbon atoms.

The semicrystalline polymer may, in at least one embodiment, be chosen from block copolymers comprising at least one crystallizable block and at least one amorphous block, homopolymers and copolymers carrying at least one crystallizable side chain per repeat unit, and blends thereof.

Such polymers are disclosed, for example, in European Patent No. 1 396 259.

According to another embodiment of the present disclosure, the at least one polymer may comprise at least one monomer comprising a crystallizable chain chosen from saturated $C_{14}$ to $C_{22}$ alkyl (meth)acrylates.

Non-limiting examples of structuring semicrystalline polymer which may be used in the composition according to the present disclosure include the Intelimer® products from Landec described in the brochure "Intelimer® polymers", Lancec IP22 (Rev. 4-97). These polymers are in a solid form at ambient temperature (25° C.).

Lipophiic Gelling Agents

The gelling agents which can be used in the compositions according to the present disclosure may also be chosen from polymeric or molecular and organic or inorganic lipophilic gelling agents.

Examples of inorganic lipophilic gelling agents may include, but are not limited to, optionally modified clays, such as hectorites modified by a $C_{10}$ to $C_{22}$ fatty acid ammonium chloride, such as hectorite modified by distearyidimethylammonium chloride, for example, the product sold under the name of Bentone 38V® by Elementis.

A further non-limiting example is pyrogenic silica optionally treated hydrophobically at the surface, the size of the particles of which is less than 1 μm. This is because it is possible to chemically modify the surface of the silica by chemical reaction, resulting in a reduction in the number of silanol groups present at the surface of the silica. It is also possible to substitute silanol groups by hydrophobic groups: a hydrophobic silica is then obtained. The hydrophobic groups may be chosen, for example, from:

trimethylsiloxyl gropus, which may be obtained by treatment of pyrogenic silica in the presence of hexamethyldisilazane. Silicas thus treated are named "Silica silylate" according to the CTFA (6th edition, 1995) and are, for example, sold under the references Aerosil R812® by Degussa and Cab-O-Sil TS-530® by Cabot, dimethylsilyloxyl or polydimethylsiloxane groups, which may be obtained by treatment of pyrogenic silica in the presence of polydimethylsiloxane or dimethyldichlorosilane. Silicas thus treated are named "Silica dimethyl silylate" according to the CTFA (6th edition, 1995), and are, for example, sold under the references Aerosil R972® and Aerosil R974® by Degussa and Cab-O-Sil TS-610® and Cab-O-Sil TS-720® by Cabot.

The hydrophobic pyrogenic silica may have a particle size which can be nanometric to micrometric, for example, ranging from approximately 5 to 200 nm.

The polymeric organic lipophilic gelling agents may be, for example, partially or completely crosslinked organopolysiloxane elastomers of three-dimensional structure, such as those sold under the names KSG6®, KSG16®, and KSG18® by Shin-Etsu, Trefil E-505C® and Trefil E-506C® by Dow-Corning, Gransil SR-CYC®, SR DMF10®, SR-DC556®, SR 5CYC gel®, SR DMF 10 gel®, and SR DC 556 gel® by Grant Industries, SF 1204® and of JK 113® by General Electric; ethylcellulose, such as that sold under the name Ethocel® by Dow Chemical; polycondensates of polyamide type resulting from the condensation between (α) at least one acid chosen from dicarboxylic acids comprising at least 32 carbon atoms, such as dimeric fatty acids, and (p) an alkylenediamine, for example, ethylenediamine, in which the polyamide polymer comprises at least one end carboxylic acid group esterified or amidated with at least one linear and saturated monoalcohol or one linear and saturated monoamine comprising from 12 to 30 carbon atoms, for example, ethylenediamine/stearyl dilinoleate copolymers, such as that sold under the name Uniclear 100 VG® by Arizona Chemical; silicone polyamides of the polyorganosiloxane type, such as those disclosed in the U.S. Pat. Nos. 5,874,069, 5,919,441, 6,051,216 and 5,981,680, for example, those sold under the references Dow Corning 2-8179 and Dow Corning 2-8178 Gellant Gellant by Dow Corning; galactomannans comprising from one to six, for instance, from two to four hydroxyl groups per monosaccharide which are substituted by a saturated or unsaturated alkyl chain, such as guar gum alkylated by $C_1$ to $C_6$ alkyl chains, for example, $C_1$ to $C_3$ alkyl chains, and mixtures thereof; block copolymers chosen from "diblock", "triblock" and "radial" block copolymers of the polystyrene/polyisoprene or polystyrene/polybutadiene type, such as those sold under the name Luvitol HSB® by BASF, of the polystyrene/copoly(ethylene-propylene) type, such as those sold under the name Kraton® by Shell Chemical Co., and of the polystyrene/copoly(ethylene-butylene) type, blends of triblock and radial (star) copolymers in isododecane, such as those sold by Penreco under the name Versagel®, for example, the blend of butylene/ethylene/styrene triblock copolymer and of ethylene/propylene/styrene star copolymer in isododecane (Versagel M 5960).

Further examples of lipophilic gelling agents which may be used in the compositions according to the present disclosure include, but are not limited to, esters of dextrin and of fatty acid, such as dextrin palmitates, such as those sold under the names Rheopearl TL® and Rheopearl KL® by Chiba Flour.

Aqueous Phase

The composition according to the present disclosure may comprise at least one aqueous medium, comprising at least one aqueous phase, which may, in at least one embodiment, form the continuous phase of the composition.

The aqueous phase may essentially comprise water; or in another embodiment, it may comprise a mixture of water and at least one water-miscible solvent (miscibility in water of greater than 50% by weight at 25° C.), such as low monoalcohols comprising from 1 to 5 carbon atoms, such as ethanol and isopropanol, glycols comprising from 2 to 8 carbon atoms, such as propylene glycol, ethylene glycol, 1,3-butylene glycol, and dipropylene glycol, $C_3$-$C_4$ ketones, $C_2$-$C_4$ aldehydes, and mixtures thereof.

The at least one aqueous phase (i.e., water and optionally at least one water-miscible solvent) may be present in the composition in an amount ranging from 1% to 95% by weight, with respect to the total weight of the composition, for example, from 3% to 80% by weight, or from 5% to 60% by weight.

Emulsifying Systems

The compositions according to the present disclosure may comprise at least one emulsifying surface-active agent present, for example, in an amount ranging from 0.1% to 20%, or from 0.3% to 15% by weight, with respect to the total weight of the composition.

According to one embodiment, the at least one emulsifier is chosen so as to obtain an oil-in-water emulsion. For example, the at least one emulsifier may have, at 25° C., an HLB (hydrophilic-lipophilic balance) value within the meaning of Griffin of greater than or equal to 8.

The HLB value according to Griffin is defined, for example, in J. Soc. Cosm. Chem., 1954 (volume 5), pages 249-256.

These surface-active agents may be chosen from noonic, anionic, cationic, and amphoteric surface-active agents and surface-active emulsifiers. The "Encyclopedia of Chemical Technology, Kirk-Othmer", volume 22, pp. 333-432, 3rd edition, 1979, Wiley, for example, provides the definition of the properties and functions (emulsifying) of surfactants, for instance, pp. 347-377 of this reference discusses anionic, amphoteric, and nonionic surfactants.

The surfactants which may be used in the composition according to the present disclosure may be chosen from:

a) nonionic surface-active agents with an HLB of greater than or equal to 8 at 25° C., and mixtures thereof, for instance:

oxyethylenated and/or oxypropylenated ethers (which may comprise from 1 to 150 oxyethylene and/or oxypropylene groups) of glycerol;

oxyethylenated and/or oxypropylenated ethers (which may comprise from 1 to 150 oxyethylene and/or oxypropylene groups) of fatty alcohols (for instance, $C_8$-$C_{24}$, or $C_{12}$-$C_{18}$, alcohols), such as the oxyethylenated ether of stearyl alcohol comprising 20 oxyethylene groups (CTFA name "Steareth-20"), such as Brij 78, sold by Uniquema, the oxyethylenated ether of cetearyl alcohol comprising 30 oxyethylene groups (CTFA name "Ceteareth-30") and the oxyethylenated ether of the mixture of $C_{12}$-$C_{15}$ fatty alcohols comprising 7 oxyethylene groups (CTFA name "C12-15 Pareth-7") sold under the name Neodol 25-7® by Shell Chemicals, esters of fatty acids (for example, $C_8$-$C_{24}$, or $C_{16}$-$C_{22}$, fatty acids) and of polyethylene glycol (which may comprise from 1 to 150 ethylene glycol units), such as PEG-50 stearate and PEG-40 monostearate, sold under the name Myrj 52P® by ICI Uniquema, esters of fatty acids (for example, $C_8$-$C_{24}$, or $C_{16}$-$C_{22}$, fatty acids) and of oxyethylenated and/or oxypropylenated glycerol ethers (which may comprise from 1 to 150 oxyethylene and/or oxypropylene groups), such as PEG-200 glyceryl monostearate, sold under the name Simulsol 220 TM® by Seppic; polyethoxylated glyceryl stearate comprising 30 ethylene oxide groups, such as the product Tagat S® sold by Goldschmidt; polyethoxylated glyceryl oleate comprising 30 ethylene oxide groups, such as the product Tagat O® sold by Goldschmidt; polyethoxylated glyceryl cocoate comprising 30 ethylene oxide groups, such as the product Varionic LI 13® sold by Sherex; polyethoxylated glyceryl isostearate comprising 30 ethylene oxide groups, such as the product Tagat L® sold by Goldschmidt; and polyethoxylated glyceryl laurate comprising 30 ethylene oxide groups, such as the product Tagat I® from Goldschmidt, esters of fatty acids (for example, $C_8$-$C_{24}$, or $C_{16}$-$C_{22}$, fatty acids) and of oxyethylenated and/or oxypropylenated sorbitol ethers (which may comprise from 1 to 150 oxyethylene and/or oxypropylene groups), such as polysorbate 60, sold under the name Tween 60® by Uniquema, dimethicone copolyols, such as that sold under the name Q2-5220® by Dow Corning, dimethicone copolyol benzoates (e.g., Finsolv SLB 101® and 201® from Fintex), copolymers of propylene oxide and of ethylene oxide, also known as EO/PO polycondensates, and mixtures thereof.

The EO/PO polycondensates may be chosen, for example, from copolymers comprising polyethylene glycol and polypropylene glycol blocks, such as polyethylene glycol/polypropylene glycol/polyethylene glycol triblock polycondensates, which, in at least one embodiment may have the following chemical structure:

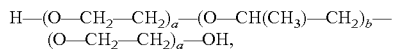

wherein a is a number ranging from 2 to 120 and b is a number ranging from 1 to 100.

The EO/PO polycondensate may have, according to one embodiment, a weight-average molecular weight ranging from 1000 to 15 000, for example, ranging from 2000 to 13 000. In another embodiment, the EO/PO polycondensate may have a cloud point, at 10 g/l in distilled water, of greater than or equal to 20° C., for instance, greater than or equal to 60° C. The cloud temperature is measured according to the standard ISO 1065. Examples of EO/PO polycondensate which may be used according to the present disclosure include, but are not limited to, the polyethylene glycol/polypropylene glycol/polyethylene glycol triblock polycondensates sold under the Synperonice names, such as Synperonic PE/L44® and Synperonic PE/F127®, by ICI, b) nonionic surface-active agents with an HLB of less than 8 at 25° C., optionally in combination with at least one nonionic surface-active agent with an HLB of greater than 8 at 25° C., such as those mentioned above, such as:

esters and ethers of monosaccharides, such as sucrose stearate, sucrose cocoate, and sorbitan stearate, and mixtures thereof, such as Arlatone 2121®, sold by ICI, and Span 65V, from Uniquema;

esters of fatty acids (for example, $C_8$-$C_{24}$, or $C_{16}$-$C_{22}$, fatty acids) and of polyols, for instance, glycerol or of sorbitol, such as glyceryl stearate, such as the product sold under the name Tegin M® by Goldschmidt, glyceryl laurate, such as the product sold under the name Imwitor 312® by Hüls, polyglyceryl-2 stearate, sorbitan tristearate, and glyceryl ricinoleate;

oxyethylenated and/or oxypropylenated ethers, such as the oxyethylenated ether of stearyl alcohol comprising 2 oxyethylene groups (CTFA name "Steareth-2"), such as Brij 72, sold by Uniquema; and the cyclomethicone/dimethicone copolyol mixture sold under the name Q2-3225C® by Dow Corning, c) anionic surfactants, such as:

salts of $C_{16}$-$C_{30}$ fatty acids, for instance, those deriving from amines, such as triethanolamine stearate;

salts of polyoxyethylenated fatty acids, such as those derived from amines and alkali metal salts, and mixtures thereof;

phosphoric esters and their salts, such as "DEA oleth-10 phosphate" (Crodafos N 10N from Croda) and monopotassium monocetyl phosphate (Amphisol K from Givaudan and Arlatone MAP 160K from Uniquema);

sulphosuccinates, such as "Disodium PEG-5 citrate lauryl sulphosuccinate" and "Disodium ricinoleamido MEA sulphosuccinate";

alkyl ether sulphates, such as sodium lauryl ether sulphate;

isethionates;

acylglutamates, such as "Disodium hydrogenated tallow glutamate" (Amisoft HS-21 R®, sold by Ajinomoto), and mixtures thereof.

Non-limiting examples of suitable cationic surfactants include:

alkyl imidazolidiniums, such as isostearyl ethylimidonium ethosulphate, and ammonium salts, such as N,N,N-trimethyl-1-docosanaminium chloride (behentrimonium chloride).

The compositions according to the present disclosure may also comprise at least one amphoteric surfactant, such as N-acylamino acids, for example N-acylaminoacetates and disodium cocoamphodiacetate, and amine oxides, such as stearamine oxide, and silicone surfactants, such as dimethicone copolyol phosphates, such as that sold under the name Pecosil PS 100® by Phoenix Chemical.

Hydrophilic Gelling Agents

The composition according to the present disclosure may comprise at least one hydrophilic gelling agent.

The hydrophilic gelling agents which may be used in the compositions according to the present disclosure may be chosen, for example, from:

homo- or copolymers of acrylic acid and methacrylic acid and their salts and esters, for example, the products sold under the names Versicol F® and Versicol K® by Allied Colloid, Ultrahold 8® by Ciba-Geigy, poly(acrylic acid)s of Synthalen K type, copolymers of acrylic acid and of acrylamide, sold in the form of their sodium salts under the Reten® names by Hercules, poly(sodium methacrylate), sold under the name Darvan No. 7® by Vanderbilt, sodium salts of poly(hydroxycarboxylic acid)s, sold under the name Hydagen F® by Henkel, copolymers of poly(acrylic acid)s and of alkyl acrylates of Pemulen type, AMPS (poly(acrylamidomethylpropanesulphonic acid)s partially neutralized with aqueous ammonia and highly crosslinked), sold by Clariant, AMPS/acrylamide copolymers of Sepigel® or Simugel® type, sold by Seppic, copolymers of AMPS and of alkyl methacrylates which are polyoxyethylenated (crosslinked or noncrosslinked), proteins, such as proteins of plant origin, such as wheat and soya proteins; proteins of animal origin, such as keratins, for example, keratin hydrolysates and sulphonic keratins;

cellulose polymers, such as hydroxyethylcellulose, hydroxypropylcellulose, methylcellulose, ethylhydroxyethylcellulose, carboxymethylcellulose, and quaternized cellulose derivatives;

acrylic polymers and copolymers, such as polyacrylates and polymethacrylates;

vinyl polymers, such as polyvinylpyrrolidones, copolymers of methyl vinyl ether and of malic anhydride, copolymers of vinyl acetate and of crotonic acid, copolymers of vinylpyrrolidone and of vinyl acetate, copolymers of vinylpyrrolidone and of caprolactam, and poly(vinyl alcohol); and optionally modified polymers of natural origin, such as:
  gums arabic, guar gum, xanthan derivatives, karaya gum, and locust bean gum;
  alginates and carrageenans (the alginates being used, in at least one embodiment, in the presence of salts, such as calcium chloride);
  glycoaminoglycans, hyaluronic acid and its derivatives;
  shellac resin, gum sandarac, dammars, elemis and copals;
  deoxyribonucleic acid; and
  mucopolysaccharides, such as chondroitin sulphates,
and mixtures thereof.

According to one embodiment, some of these water-soluble gelling agents may also act as film-forming polymers.

The at least one water-soluble gelling polymer may be present in the composition in a dry matter content ranging from 0.01% to 30%, for example, from 0.05% to 20%, or from 0.1% to 10% by weight, with respect to the total weight of the composition.

The compositions of the present disclosure may also comprise ingredients commonly used in the field of making up the eyelashes.

Waxes

The composition according to the present disclosure may comprise at least one wax.

The at least one may generally be characterized as a lipophilic compound which is solid at ambient temperature (25° C.), which exhibits a reversible solid/liquid change in state, and which has a melting point of greater than or equal to 30° C., which can range up to 200° C., for instance, up to 120° C.

On bringing the wax to the liquid state (melting), it is possible to render it miscible with oils and to form a microscopically homogeneous mixture but, on bringing the temperature of the mixture back to ambient temperature, recrystallization of the wax in the oils of the mixture may be obtained.

In one embodiment, the at least one wax suitable for use in the compositions of the present disclosure may have a melting point of greater than or equal to 45° C., for example, greater than or equal to 55° C.

As used herein, the term "melting point" denotes the temperature of the most endothermic peak observed by thermal analysis (DSC) as described in the standard ISO 11357-3; 1999. The melting point of the wax can be measured using a differential scanning calorimeter (DSC), for example the calorimeter sold under the name "MDSC 2920" by TA Instruments.

The measurement protocol is as follows:

A 5 mg sample of wax placed in a crucible is subjected to a first rise in temperature ranging from −20° C. to 100C at a heating rate of 10° C./minute, is then cooled from 100° C. to −20° C. at a cooling rate of 10° C./minute and, finally, is subjected to a second rise in temperature ranging from −20° C. to 100° C. at a heating rate of 5° C./minute. During the second rise in temperature, the variation in the difference in power absorbed by the empty crucible and by the crucible comprising the sample of wax is measured as a function of the temperature. The melting point of the compound is the value of the temperature corresponding to the tip of the peak of the curve representing the variation in the difference in power absorbed as a function of the temperature.

The at least one wax suitable for use in the compositions according to the present disclosure may be chosen, for example, from animal waxes, vegetable waxes, mineral waxes, synthetic waxes, and mixtures thereof, which are solid at ambient temperature.

The waxes which may be used in the compositions according to the present disclosure may generally exhibit a hardness ranging from 0.01 MPa to 15 MPa, for example, greater than 0.05 MPa, or greater than 0.1 MPa.

The hardness is determined by the measurement of the compressive force measured at 20° C. using a texture analyser sold under the name TA-XT2 by Rheo, equipped with a stainless steel cylinder with a diameter of 2 mm which is displaced at the measuring rate of 0.1 mm/s and which penetrates the wax to a penetration depth of 0.3 mm.

The measurement protocol is as follows:

The wax is melted at a temperature equal to the melting point of the wax +10° C. The molten wax is cast in a receptacle with a diameter of 25 mm and a depth of 20 mm. The wax is recrystallized at ambient temperature (25° C.) for 24 hours, so that the surface of the wax is flat and smooth, and then the wax is stored at 20° C. for at least one hour before measuring the hardness or the tack.

The rotor of the texture analyser is displaced at a rate of 0.1 mm/s and then penetrates the wax to a penetration depth of 0.3 mm. When the rotor has penetrated the wax to the depth of 0.3 mm, the rotor is held stationary for 1 second (corresponding to the relaxation time) and is then withdrawn at the rate of 0.5 mm/s.

The value of the hardness is the maximum compressive force measured divided by the surface area of the cylinder of the texture analyser in contact with the wax.

Examples of waxes suitable for use in the compositions of the present disclosure include hydrocarbon waxes, such as beeswax, lanolin wax, and Chinese insect waxes; rice bran wax, carnauba wax, candelilla wax, ouricury wax, alfa wax, berry wax, shellac wax, Japan wax, and sumac wax; montan wax, orange and lemon waxes, microcrystalline waxes, paraffin waxes, and ozokerite; polyethylene waxes, the waxes obtained by the Fischer-Tropsch synthesis and waxy copolymers, and their esters.

Other suitable waxes include, for example, waxes obtained by catalytic hydrogenation of animal or vegetable oils comprising linear or branched $C_8$-$C_{32}$ fatty chains, for instance, isomerized jojoba oil, such as the transisomerized partially hydrogenated jojoba oil manufactured or sold by Desert Whale under the commercial reference Iso-Jojoba-50®, hydrogenated sunflower oil, hydrogenated castor oil, hydrogenated coconut oil, hydrogenated lanolin oil, and di(1,1,1-trimethylolpropane) tetrastearate, sold under the name of Hest 2T-4S® by Heterene.

In at least one embodiment, silicone waxes and fluorinated waxes may also be used.

Further non-limiting examples include waxes obtained by hydrogenation of castor oil esterified with cetyl alcohol which are sold under the names of Phytowax Castor 16L64® and 22L73° by Sophim. Such waxes are disclosed, for instance, in French Patent Application No. 2 792 190.

According to one embodiment, the compositions according to the present disclosure may comprise at least one wax referred to as a "tacky wax", i.e., a wax having a tack of greater than or equal to 0.1 N.s and a hardness of less than or equal to 3.5 MPa.

The at least one tacky wax may have a tack ranging from 0.1 N.s to 10 N.s, for example, ranging from 0.1 N.s to 5 N.s, from 0.2 to 5 N.s, or from 0.3 to 2 N.s.

The tack of the wax is determined by the measurement of the change in the force (compressive force) as a function of the time at 20° C. according to the protocol indicated above for the hardness.

During the relaxation time of 1 s, the force (compressive force) strongly decreases until it becomes zero and then, during the withdrawal of the rotor, the force (stretching force) becomes negative to subsequently again increase towards the value 0. The tack corresponds to the integral of the curve of the force as a function of the time for the part of the curve corresponding to the negative values of the force. The value of the tack is expressed in N.s.

The at least one tacky wax which may be used in the compositions of the present disclosure generally has a hardness of less than or equal to 3.5 MPa, for instance, ranging from 0.01 MPa to 3.5 MPa, or from 0.05 MPa to 3 MPa.

Non-limiting examples of a suitable tacky waxes include $C_{20}$-$C_{40}$ alkyl (hydroxystearyloxy)stearates (the alkyl group comprising from 20 to 40 carbon atoms) and mixtures thereof.

Such a wax is sold, for example, under the names "Kester Wax K 82 P®", "Hydroxypolyester K 82 P®" and "Kester Wax K 80 P®" by Koster Keunen.

The at least one wax may, in at least one embodiment, be chosen from waxes provided in the form of small particles having a size, expressed as volume-average "effective" diameter D[4,3], ranging from 0.5 to 30 micrometers, for example, from 1 to 20 micrometers, or from 5 to 10 micrometers, subsequently denoted by the expression "microwaxes".

The sizes of the particles can be measured by various techniques, for instance, light scattering techniques (dynamic and static), Coulter counter methods, measurements by rate of sedimentation (related to the size via Stokes' law), and microscopy. These techniques make it possible to measure a particle diameter and, for some of them, a particle size distribution.

In one embodiment, the sizes and size distributions of the particles of waxes are measured by static light scattering using a commercial particle sizer of MasterSizer 2000 type from Malvern. The data are processed on the basis of the Mie scattering theory. This theory, exact for isotropic particles, makes it possible to determine, in the case of nonspherical particles, an "effective" particle diameter. This theory is described, for example, in the work by Van de Hulst, H. C., "Light Scattering by Small Particles", Chapters 9 and 10, Wiley, New York, 1957.

The size is expressed by the mean "effective" diameter by volume D[4,3], defined in the following way:

$$D[4,3] = \frac{\sum_i V_i \cdot d_i}{\sum_i V_i}$$

where $V_i$ is the volume of the particles with an effective diameter $d_i$. This parameter is described in the technical documentation of the particle sizer.

The "effective" diameter is obtained by taking a refractive index of 1.33 for the water and a mean refractive index of 1.42 for the particles.

Examples of suitable microwaxes which may be used in the compositions according to the present disclosure include, but are not limited to, carnauba microwaxes, such as that sold under the name of MicroCare 350® by Micro Powders, synthetic wax microwaxes, such as that sold under the name of MicroEase 114S® by Micro Powders, microwaxes comprising a mixture of carnauba wax and of polyethylene wax, such as those sold under the names of MicroCare 300 and 310® by Micro Powders, microwaxes composed of a mixture of carnauba wax and of synthetic wax, such as that sold under the name MicroCare 325® by Micro Powders, polyethylene microwaxes, such as those sold under the names of Micropoly 200®, 220®, 220L® and 250S® by Micro Powders, and polytetrafluoroethylene microwaxes, such as those sold under the names of Microslip 519® and 519 L® by Micro Powders.

The at least one wax may be present in the composition according to the present disclosure in an amount ranging from 0.1 to 50% by weight, with respect to the total weight of the composition, for example, from 0.5 to 35% by weight.

Film-Forming Polymers

The composition according to the present disclosure may also comprise at least one film-forming polymer.

The at least one film-forming polymer may be present in the composition according to the present disclosure in a dry matter (or active materials) content ranging from 0.1% to 30% by weight, with respect to the total weight of the composition, for example, from 0.5% to 20% by weight, or from 1% to 15% by weight.

As used herein, the term "film-forming polymer" is understood to mean a polymer capable of forming, by itself alone or in the presence of an additional agent which is able to form a film, a macroscopically continuous film which adheres to the eyelashes, for instance, a cohesive film, and in at least one embodiment, a film possessing a cohesion and mechanical properties such that the film may be able to be isolated and to be handled in isolation, for example, when the film is produced by casting over a non-stick surface, such as a Teflon or silicone surface.

Non-limiting examples of film-forming polymers which may be used in the composition of the present disclosure include synthetic polymers of radical type, synthetic polymers of polycondensate type, polymers of natural origin, and mixtures thereof.

As used herein, the term "radical film-forming polymer" is understood to mean a polymer obtained by polymerization of monomers possessing unsaturation, for instance, ethylenic unsaturation, each monomer being capable of homopolymerizing (unlike polycondensates).

The film-forming polymers of radical type may be chosen, for example, from vinyl polymers and copolymers, such as acrylic polymers.

The film-forming vinyl polymers may result from the polymerization of monomers possessing ethylenic unsaturation comprising at least one acid group and/or of the esters of these acidic monomers and/or of the amides of these acidic monomers.

Examples of monomers comprising at least one acid group include, but are not limited to, unsaturated α,β-ethylenic carboxylic acids, such as acrylic acid, methacrylic acid, crotonic acid, maleic acid, and itaconic acid. In at least one embodiment, the monomer is chosen from (meth)acrylic acid and crotonic acid, and in another embodiment, the monomer is (meth)acrylic acid.

Suitable esters of acidic monomers may be chosen, for example, from esters of (meth)acrylic acid (also known as (meth)acrylates), such as alkyl (meth)acrylates, for instance, $C_1$-$C_{30}$ alkyl (meth)acrylates, such as $C_1$-$C_{20}$ alkyl (meth)acrylates, aryl (meth)acrylates, for instance, $C_6$-$C_{10}$ aryl (meth)acrylates, and hydroxyalkyl (meth)acrylates, for example, $C_2$-$C_6$ hydroxyalkyl (meth)acrylates.

Examples of alkyl (meth)acrylates include, but are not limited to, methyl methacrylate, ethyl methacrylate, butyl methacrylate, isobutyl methacrylate, 2-ethylhexyl methacrylate, lauryl methacrylate, and cyclohexyl methacrylate.

Hydroxyalkyl (meth)acrylates may include, for instance, hydroxyethyl acrylate, 2-hydroxypropyl acrylate, hydroxyethyl methacrylate, and 2-hydroxypropyl methacrylate.

Non-limiting examples of aryl (meth)acrylates include benzyl acrylate and phenyl acrylate.

According to at least one embodiment, the esters of (meth) acrylic acid may be chosen from alkyl (meth)acrylates.

According to another embodiment, the alkyl group of the esters may be either fluorinated or perfluorinated, i.e., a portion or all of the hydrogen atoms of the alkyl group may be substituted by fluorine atoms.

Suitable amides of the acidic monomers may include, for example, (meth)acrylamides, for instance, N-alkyl(meth)acrylamides, such as N—($C_2$-$C_{12}$ alkyl)-(meth)acrylamides, for example, N-alkyl(meth)acrylamides, N-ethylacrylamide, N-(t-butyl)-acrylamide, N-(t-octyl)acrylamide, and N-undecylacrylamide.

The film-forming vinyl polymers may also result from the homopolymerization or from the copolymerization of monomers chosen from vinyl esters and styrene monomers. In one embodiment, these monomers may be polymerized with acidic monomers and/or their esters and/or their amides, such as those mentioned above.

Examples of vinyl esters include, but are not limited to, vinyl acetate, vinyl neodecanoate, vinyl pivalate, vinyl benzoate, and vinyl t-butylbenzoate.

Suitable styrene monomers may be chosen, for instance, from styrene and α-methylstyrene.

Film-forming polycondensates may include, for example, polyurethanes, polyesters, polyesteramides, polyamides, epoxy ester resins, and polyureas.

In at least one embodiment, the polyurethanes may be chosen from anionic, cationic, nonionic, and amphoteric polyurethanes, polyurethane-acrylics, polyurethane-polyvinylpyrrolidones, polyester-polyurethanes, polyether-polyurethanes, polyureas, polyurea-polyurethanes, and blends thereof.

According to another embodiment, the polyesters may be obtained in a known way by polycondensation of dicarboxylic acids with polyols, such as diols.

The dicarboxylic acid may be chosen from aliphatic, alicyclic, and aromatic acids, for example, oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid, and 2,6-naphthalenedicarboxylic acid. These dicarboxylic acid monomers may be used alone or as a combination of at least two dicarboxylic acid monomers. In at least one embodiment, the dicarboxylic acid may be chosen from phthalic acid, isophthalic acid, and terephthalic acid.

According to another embodiment, the diol may be chosen from aliphatic, alicyclic, and aromatic diols. In yet another embodiment, the diol may be chosen from ethylene glycol, diethylene glycol, triethylene glycol, 1,3-propanediol, cyclohexanedimethanol, and 1,4-butanediol. Other suitable polyols may include, for example, glycerol, pentaerythritol, sorbitol, and trimethylolpropane.

The polyesteramides may be obtained in an analogous way to the polyesters, by polycondensation of diacids with diamines or aminoalcohols.

Suitable diamines may include, for instance, ethylenediamine, hexamethylenediamine, meta-phenylenediamine, and para-phenylenediamine. In at least one embodiment, the aminoalcohol may be monoethanolamine.

The polyester may additionally comprise at least one monomer carrying at least one —$SO_3M$ group, wherein M is chosen from hydrogen, $NH_4^+$ ammonium ions, and metal ions, such as $Na^+$, $Li^+$, $K^+$, $Mg^{2+}$, $Ca^{2+}$, $Cu^{2+}$, $Fe^{2+}$, and $Fe^{3+}$ ions. According to one embodiment, the monomer may be a bifunctional aromatic monomer comprising such an —$SO_3M$ group.

The aromatic nucleus of the bifunctional aromatic monomer additionally carrying an —$SO_3M$ group as described above may be chosen, for example, from benzene, naphthalene, anthracene, diphenyl, oxydiphenyl, sulphonyidiphenyl, and methylenediphenyl nuclei. Examples of bifunctional aromatic monomers additionally carrying an —$SO_3M$ group include, but are not limited to, sulphoisophthalic acid, sulphoterephthalic acid, sulphophthalic acid, and 4-sulphonaphthalene-2,7-dicarboxylic acid.

In at least one embodiment, copolymers based on isophthalate/sulphoisophthalate and copolymers obtained by condensation of diethylene glycol, cyclohexanedimethanol, isophthalic acid, and sulphoisophthalic acid may be used.

The optionally modified polymers of natural origin may be chosen, for example, from shellac resin, gum sandarac, dammars, elemis, copals, cellulose polymers, and blends thereof.

According to one embodiment, the at least one film-forming polymer may be a water-soluble polymer and may be present in an aqueous phase of the composition; the polymer may thus be dissolved in the aqueous phase of the composition.

According to another embodiment, the at least one film-forming polymer may be a polymer dissolved in a liquid fatty phase comprising oils and/or organic solvents, such as those described above (the film-forming polymer is then described as a fat-soluble polymer). In yet another embodiment, the liquid fatty phase comprises a volatile oil, optionally as a mixture with a non-volatile oil, it being possible for the oils to be chosen from the oils mentioned above.

Examples of fat-soluble polymers include, but are not limited to, copolymers of vinyl ester (the vinyl group being directly connected to the oxygen atom of the ester group and the vinyl ester having a saturated, linear or branched, hydrocarbon radical comprising from 1 to 19 carbon atoms bonded to the carbonyl of the ester group) and of at least one other monomer which may be chosen from vinyl esters (other than the vinyl ester already present), α-olefins (comprising from 8 to 28 carbon atoms), alkyl vinyl ethers (the alkyl group of which comprises from 2 to 18 carbon atoms), and allyl or methallyl esters (comprising a saturated, linear or branched, hydrocarbon radical comprising from 1 to 19 carbon atoms bonded to the carbonyl of the ester group).

These copolymers may optionally be crosslinked using crosslinking agents which may be chosen from vinyl, allyl, and methallyl crosslinking agents, such as tetraallyloxyethane, divinylbenzene, divinyl octanedioate, divinyl dodecanedioate, and divinyl octadecanedioate.

Non-limiting examples of these copolymers include vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% of divinylbenzene, vinyl dimethylpropionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene, crosslinked with 0.2% of divinylbenzene, and allyl propionate/allyl stearate, crosslinked with 0.2% of divinylbenzene.

Fat-soluble film-forming polymers may include, for instance, fat-soluble copolymers, such as those resulting from the copolymerization of vinyl esters comprising from 9 to 22 carbon atoms or of alkyl acrylates or methacrylates, the alkyl radicals comprising from 10 to 20 carbon atoms.

Such fat-soluble copolymers may be chosen, for example, from copolymers of poly(vinyl stearate), copolymers of poly (vinyl stearate) crosslinked using an agent chosen from divinylbenzene, diallyl ether, and diallyl phthalate, copolymers of poly(stearyl (meth)acrylate), copolymers of poly(vinyl laurate), and copolymers of poly(lauryl (meth)acrylate), it being possible for these poly(meth)acrylates to be crosslinked using an agent chosen from ethylene glycol dimethacrylate and tetraethylene glycol dimethacrylate.

The fat-soluble copolymers defined above are known in the art and are disclosed, for instance, in French Patent Application No. 2 232 303; and may have a weight-average molecular weight ranging from 2000 to 500 000, for example, from 4000 to 200 000.

Further non-limiting examples of fat-soluble film-forming polymers include polyalkylenes, for instance, copolymers of $C_2$-$C_{20}$ alkenes, such as polybutene, alkylcelluloses comprising a saturated or unsaturated and linear or branched $C_1$ to $C_8$ alkyl radicals, such as ethylcellulose and propylcellulose, copolymers of vinylpyrrolidone (VP), such as copolymers of vinylpyrrolidone and of $C_2$ to $C_{40}$ alkenes, for example, $C_3$ to $C_{20}$ alkenes. Examples of suitable VP copolymers include, but are not limited to, VP/vinyl acetate, VP/ethyl methacrylate, VP/ethyl methacrylate/methacrylic acid, VP/eicosene, VP/hexadecene, VP/triacontene, VP/styrene, VP/acrylic acid/lauryl methacrylate copolymer, and butylated polyvinylpyrrolidone (PVP).

Silicone resins, generally soluble or swellable in silicone oils, which are crosslinked polyorganosiloxane polymers may also be used. The nomenclature of silicone resins is known under the name of "MDTQ", the resin being described according to the various siloxane monomer units which it comprises, each of the letters "MDTQ" characterizing one type of unit.

Examples of commercially available polymethylsilsesquioxane resins include, but are not limited to, those which are sold:

by Wacker under the reference Resin MK, such as Belsil PMS MK; and by Shin-Etsu under the references KR-220L.

Siloxysilicate resins may include, for instance, trimethylsiloxysilicate (TMS) resins, such as those sold under the reference SR1000 by General Electric or under the reference TMS 803 by Wacker; and trimethylsiloxysilicate resins sold in a solvent, such as cyclomethicone, sold under the names "KF-7312J" by Shin-Etsu and "DC 749" and "DC 593" by Dow Corning.

Further examples include, but are not limited to, copolymers of silicone resins, such as those mentioned above with polydimethylsiloxanes, such as the pressure-sensitive adhesive copolymers sold by Dow Corning under the reference BIO-PSA and disclosed in U.S. Pat. No. 5,162,410 or the silicone copolymers resulting from the reaction of a silicone resin, such as those described above, and of a diorganosiloxane, such as those disclosed in International Patent Application Publication No. WO 2004/073626.

According to one embodiment, the at least one film-forming polymer is a film-forming linear block ethylenic polymer which may comprise at least one first block and at least one second block having different glass transition temperatures (Tg), the first and second blocks being connected to one another via an intermediate block comprising at least one constituent monomer of the first block and at least one constituent monomer of the second block.

In another embodiment, the first and second blocks of the block polymer are incompatible with one another.

Such polymers are disclosed, for example, in European Patent No. 1 411 069 and International Patent Application Publication No. WO04/028488.

The at least one film-forming polymer may also be present in the composition in the form of particles in dispersion in a phase chosen from aqueous phases and nonaqueous solvent phases, generally known under the name of latex or pseudolatex. The techniques for the preparation of these dispersions are known to a person skilled in the art.

Non-limiting examples of suitable aqueous film-forming polymer dispersions include acrylic dispersions, sold under the names Neocryl XK-90®, Neocryl A-1070®, Neocryl A-1090®, Neocryl BT-62®, Neocryl A-1079®, and Neocryl A-523 by Avencia Neoresins, Dow Latex 432® by Dow Chemical, Daitosol 5000 AD® and Daitosol 5000 SJ® by Daito Kasey Kogyo; Syntran 5760 by Interpolymer, Allianz OPT by Röhm & Haas, aqueous dispersions of acrylic or styrene/acrylic polymers, sold under the trade name Joncryl® by Johnson Polymer, and aqueous dispersions of polyurethane, sold under the names Neorez R-981® and Neorez R-974® by Avecia-Neoresins, Avalure UR-405®, Avalure UR-410®, Avalure UR-425®, Avalure UR-450®, Sancure 875®, Sancure 861®, Sancure 878®, and Sancure 2060® by Goodrich, Impranil 85® by Bayer, Aquamere H-1511® by Hydromer; sulphopolyesters, sold under the trade name Eastman AQ® by Eastman Chemical Products, vinyl dispersions, such as Mexomer PAM® from Chimex, and blends thereof.

Examples of nonaqueous dispersions of film-forming polymer include, but are not limited to, acrylic dispersions in isododecane, such as Mexomer PAP® from Chimex, dispersions of particles of a grafted ethylenic polymer, for example, an acrylic polymer, in a liquid fatty phase, the ethylenic polymer optionally being dispersed in the absence of additional stabilizer at the surface of the particles, such as those disclosed, for example, in International Patent Application Publication No. WO 04/055081.

The composition according to the present disclosure may comprise a plasticizing agent favorable to the formation of a film with the film-forming polymer. Such a plasticizing agent can be chosen from any compound known to a person skilled in the art as being capable of fulfilling the desired role.

Coloring Materials

The composition according to the present disclosure may also comprise at least one coloring material, such as pulverulent materials, fat-soluble dyes, and water-soluble dyes.

The pulverulent coloring materials may be chosen, for example, from pigments and pearlescent agents.

The pigments may be white or colored, inorganic and/or organic, and coated or noncoated. Examples of inorganic pigments include, but are not limited to, titanium dioxide, optionally treated at the surface, zirconium, zinc oxides, cerium oxides, iron oxides, chromium oxides, manganese violet, ultramarine blue, chromium hydrate, and ferric blue. Non-limiting examples of organic pigments include carbon black, pigments of D & C type and lakes, based on cochineal carmine, of barium, strontium, calcium, and aluminum.

The pearlescent agents may be chosen, for instance, from white pearlescent pigments, such as mica covered with titanium oxide and mica covered with bismuth oxychloride, colored pearlescent pigments, such as titanium oxide-coated mica with iron oxides, titanium oxide-coated mica with, for example, ferric blue and/or chromium oxide, titanium oxide-coated mica with an organic pigment of the abovementioned type, and pearlescent pigments based on bismuth oxychloride.

The fat-soluble dyes include, for example, Sudan red, D&C Red 17, D&C Green 6, β-carotene, soybean oil, Sudan brown, D&C Yellow 11, D&C Violet 2, D&C Orange 5, quinoline yellow, and annatto.

The at least one coloring material may be present in an amount ranging from 0.01 to 30% by weight, with respect to the total weight of the composition.

Fillers

The composition according to the present disclosure may additionally comprise at least one filler.

The fillers may be chosen from those known to a person skilled in the art and commonly used in cosmetic compositions. The fillers may be inorganic or organic and lamellar or spherical. Non-limiting examples include talc, mica, silica, kaolin, powders of polyamide, such as Nylon®, sold under the name Orgasol® by Atochem, of poly-β-alanine and of polyethylene, powders formed of tetrafluoroethylene polymers, such as Teflon®, lauroyllysine, starch, boron nitride, expanded polymer hollow microspheres, such as those of poly(vinylidene chloride)/acrylonitrile, such as those sold under the name of Expancel® by Nobel Industrie, acrylic powders, such as those sold under the name Polytrap® by Dow Corning, poly(methyl methacrylate) particles and silicone resin microbeads (Tospearls®) from Toshiba, for example), precipitated calcium carbonate, magnesium carbonate, basic magnesium carbonate, hydroxyapatite, hollow silica microspheres (Silica Beads® from Maprecos), glass or ceramic microcapsuies, and metal soaps derived from organic carboxylic acids comprising from 8 to 22 carbon atoms, for instance, from 12 to 18 carbon atoms, for example zinc stearate, magnesium stearate, lithium stearate, zinc laurate, and magnesium myristate.

The at least one filler may also be chosen from compounds capable of swelling when heated, for example, heat-expandable particles, such as nonexpanded microspheres of vinylidene chloride/acrylonitrile/methyl methacrylate copolymer and microspheres of copolymer or homopolymer of acrylonitrile, such as those sold respectively under the references Expancel® 820 DU 40 and Expancel® 007WU by Akzo Nobel.

The at least one filler may be present in the composition in an amount ranging from 0.1 to 25%, for example, from 1 to 20%, by weight, with respect to the total weight of the composition.

The composition of the present disclosure may additionally comprise at least one additive conventionally used in cosmetics, such as antioxidants, preservatives, fibers, fragrances, neutralizing agents, gelling agents, thickeners, vitamins, coalescence agents, plasticizers, and mixtures thereof.

Fibers

The composition according to the present disclosure may additionally comprise at least one fiber, which may make possible an improvement in the lengthening effect.

As used herein, the term "fiber" is understood as meaning an object with a length L and a diameter D such that L is much greater than D, D being the diameter of the circle in which the cross section of the fiber is framed. In at least one embodiment, the L/D ratio (or aspect ratio) may range from 3.5 to 2500, for example, from 5 to 500, or from 5 to 150.

The fibers which may be used in the composition of the present disclosure may be chosen from synthetic or natural and inorganic or organic fibers. They may be short or long, individual or organized, for example plaited, and hollow or solid. They may have any shape and, in at least one embodiment, may be circular or polygonal (for example, square, hexagonal, and octagonal) in cross section, according to the specific application envisaged. In one embodiment, the ends of the fibers may be blunted and/or polished to prevent injury.

In another embodiment, the fibers may have a length ranging from 1 μm to 10 mm, for instance, from 0.1 mm to 5 mm, or from 0.3 mm to 3.5 mm. Their cross section may be included within a circle with a diameter ranging from 2 nm to 500 μm, for example, ranging from 100 nm to 100 μm, or from 1 μm to 50 μm. The weight or count of the fibers is often given in denier or decitex and represents the weight in grams per 9 km of yarn. The fibers according to the present disclosure may have a count ranging from 0.15 to 30 denier, for instance, from 0.18 to 18 denier.

The fibers which may be used in the composition of the present disclosure may be chosen from rigid and nonrigid fibers. The fibers may be of synthetic or natural and inorganic or organic origin.

Furthermore, the fibers may or may not be surface treated, may or may not be coated, and may or may not be colored.

Non-limiting examples of fibers which may be used in the composition according to the present disclosure include fibers which are not rigid, such as polyamide (Nylon®) fibers, and fibers which are rigid, such as polyimideamide fibers, for example those sold under the Kermel® and Kermel Tech® names by Rhodia, and poly(p-phenylene tereph-thalamide) (or aramid) fibers, sold, for instance, under the Kevlar® name by DuPont de Nemours.

The at least one fiber may be present in the composition according to the present disclosure in an amount ranging from 0.01% to 10% by weight, with respect to the total weight of the composition, for example, from 0.1% to 5% by weight, or from 0.3% to 3% by weight.

Cosmetic Active Principles

The compositions of the present disclosure may include at least one cosmetic active principle, such as antioxidants, preservatives, fragrances, neutralizing agents, emollients, moisturizing agents, vitamins, and screening agents, and in at least one embodiment, sunscreens.

It is to be understood that a person skilled in the art will take care to choose the at least one optional additional additive and/or the amounts thereof such that the advantageous properties of the composition according to the present disclosure are not, or are not substantially, detrimentally affected by the envisaged addition.

Preparation Process

The compositions employed in the present disclosure may be prepared by processes for mixing, stirring, and/or dispersing compressed gases, such as air, chlorofluorocarbon-based compounds, nitrogen, carbon dioxide, oxygen, and helium, liquefied gases, such as liquefied petroleum gases, and processes for mixing and stirring in the presence of at least one foaming agent, such as a surfactant.

In at least one embodiment, the composition may be prepared by mixing the ingredients with stirring, generally under hot conditions, and by then expanding in volume under the action of a gas, it being possible for the gas to be introduced during the stage of cooling the composition or after preparation of the composition, for example, using a device for expanding in volume of Mondomix type, a beater of Kenwood type, a scraped-surface exchanger or a dynamic mixer (of IMT type, for example). According to at least one embodiment, the gas may be chosen from air and nitrogen.

The composition before expanding in volume may be provided in a form chosen from suspensions, dispersions, solutions, gels, and emulsions, such as oil-in-water (O/W), wax-in-water, water-in-oil (W/O), and multiple (W/O/W, polyol/O/W, and O/W/O) emulsions. In one embodiment, the composition may be anhydrous.

Kits

The composition according to the present disclosure may be packaged in a container comprising at least one compartment which comprises a composition of the present disclosure, the container being closed by a closure part. The container may be equipped with a means for the dispensing of the product, for example, the container can be equipped with a pump. In an alternative form, it can be equipped with a valve, the product then being packaged under pressure inside the container. In the cases where the container is equipped with a dispensing means, the presentation of the product in the foam form may be obtained at the time of the dispensing thereof.

The container may be at least partly made of a thermoplastic, for example, polypropylene and polyethylene. In an alternative embodiment, the container may be made of a nonthermoplastic, such as glasses, metals, and metal alloys.

In at least one embodiment, the container may be used in combination with an applicator comprising at least one application component configured to apply the composition to the eyelashes.

Thus, disclosed herein is a kit for making up and/or for the nontherapeutic care of the eyelashes comprising:

a container comprising a composition in the form of a foam and having a density of less than or equal to 0.95 g/cm³ and an applicator comprising at least one application component configured to apply the composition to the eyelashes.

In at least one embodiment, the applicator may be an applicator of fingerstall type, provided in order to be put on at the end of a finger and comprises a surface condition exhibiting projection-forming embossments. These embossments may be positioned uniformly on the surface. They may be separated by a mean distance ranging, for example, from 0.5 to 1 mm. These projection-forming embossments may have a height of 1 mm, relative to the surface from which they protrude.

To withdraw the product in the foam form, the user may immerse these embossments therein from time to time. The product may be retained between these embossments and may subsequently be applied to a line of eyelashes, the embossments participating in the spreading and in the combing of these eyelashes.

According to another embodiment, the applicator may comprise an application nozzle.

An embodiment of an applicator 1 capable of being used for the application of a composition in the foam form according to the present disclosure is represented in FIG. 1. This applicator 1 comprises an applicator nozzle 2 mounted at the end of a grasping means 3. This applicator 1 may be put away, when not being used, in a housing 4 of a closure means 5 of a container 6 comprising the product to be applied. The applicator nozzle 2 may be mounted in a detachable fashion on the grasping means 3 so as to be able to be changed. The housing 4 may comprise a wringer. It may also comprise an impregnated seat intended to be brought into contact with the nozzle 2 to prevent it from drying out or to allow it to be cleaned, between two uses.

In this embodiment, the container 6 is a cylindrical jar such that the closure means 5 is fitted by screwing onto a neck of this container. For example, the screwing of the closure means 5 may be carried out about an axis Y perpendicular to a plane in which an opening of the container 6 is defined. The housing 4 may be configured to receive at least the applicator nozzle 2 which is, in this embodiment, oriented according to an oblique axis Z relative to the axis Y. The introduction of the applicator 1 into its housing 4 may be obtained, for example, by translation. The retention of the applicator in its housing 4 may be obtained, for example, by latching by interaction between the grasping means 3 and the closure means 5.

In at least one embodiment, the applicator nozzle 2 comprises a longitudinal axis X such that the insertion of the applicator 1 in its housing 4 may be carried out by translation along this axis X, so that, in the put-away position, the axis Z of the housing 4 and the axis X of the applicator nozzle 2 are substantially parallel.

The applicator nozzle 2 may be, for example, made of a porous material. According to one embodiment, the application surface defined by this applicator nozzle may be configured in order to retain a product presented in the foam form, without denaturing the structure thereof, when the nozzle is brought into contact with a surface of this product or at least slightly immersed in the product.

The applicator nozzle 2 may be produced from an elastically deformable material. It may be produced from an elastomer, from a sintered product, from a felt, and/or from a foam. As used herein, the term "felt" means a fibrous structure comprising filaments entangled in all directions. The foam is a cellular structure which may comprise, at its surface, dimples which make it possible to store and retain an amount of product at the surface, it being possible for these dimples to be distributed uniformly or nonuniformly at the surface. The foam may have cells chosen from open, semi-open, and closed cells. In at least one embodiment, the diameter of the dimples at the surface of the applicator nozzle 2 are substantially equal to or greater than the mean diameter of the air bubbles formed in the product in the foam form.

The foam of the applicator nozzle may, for example, be produced from at least one of the material chosen, for example, from polyurethane, polyether, polyester, poly(vinyl chlorides and EVA.

The applicator nozzle 2 may be covered with a flock coating, for example deposited on a layer of a thermoplastic. The flock coating may, for example, comprise bristles which are different in diameter and/or nature and/or height or of a mixture of such bristles. The applicator nozzle 2 may be covered with a woven material or with a nonwoven material or with any other covering exhibiting embossments towards the outside, for example, hooks or loops projecting towards the outside of the covering.

The applicator nozzle 2 may be a multilayer structure comprising a layer defining an application surface and at least one lower layer intended, for example, to confer more or less high stiffness or flexibility on the applicator nozzle and/or to improve the ability of the applicator to absorb product.

The applicator nozzle 2 may be, for example, tubular in shape with a circular cross section. In the alternative forms represented in FIGS. 2 to 5, without departing from the scope of the present disclosure, the cross section of the applicator nozzle 2 may also be oval or polygonal, for example, triangular, square, or rectangular.

A free end 7 of this applicator nozzle 2, opposite the end of the nozzle held in the grasping member 3, may be substantially defined in a plane. This free end 7 may define at least in part a surface intended to be charged with product and to be brought into contact with the eyelashes.

Figure 2:
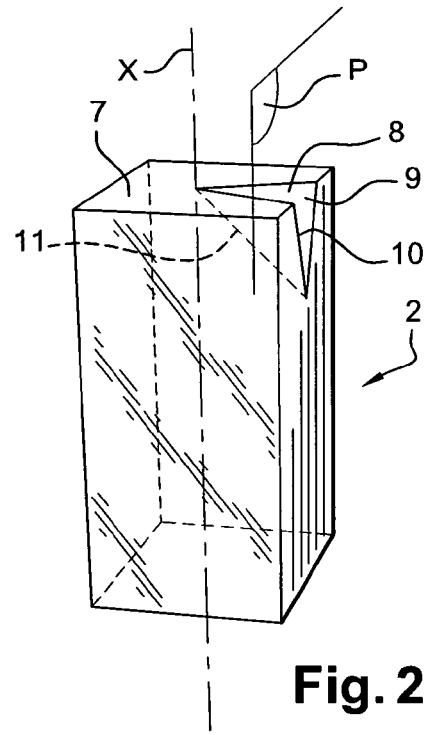
FIG. 2 illustrates a second embodiment of an applicator suitable for use in the kits of the present disclosure.
Figure 3:
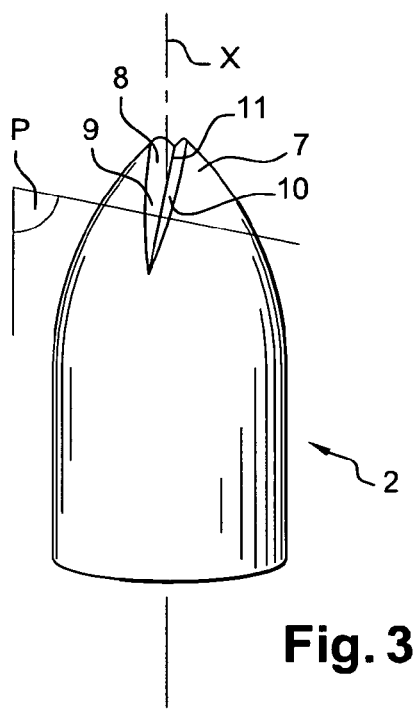
FIG. 3 illustrates a third embodiment of an applicator suitable for use in the kits of the present disclosure.
Figure 4:
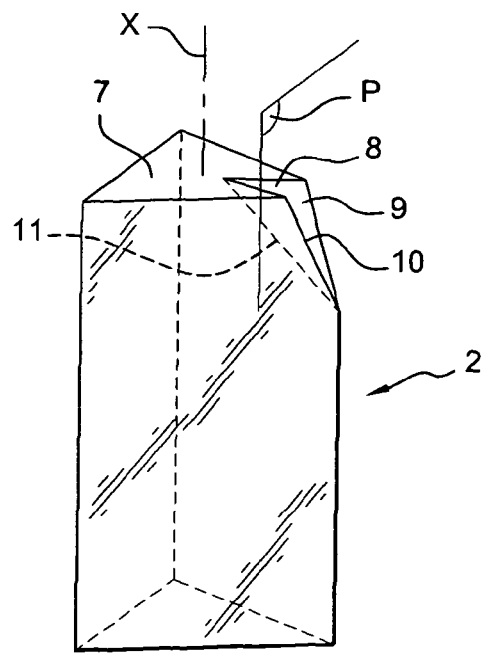
FIG. 4 illustrates a fourth embodiment of an applicator suitable for use in the kits of the present disclosure.
Figure 5:
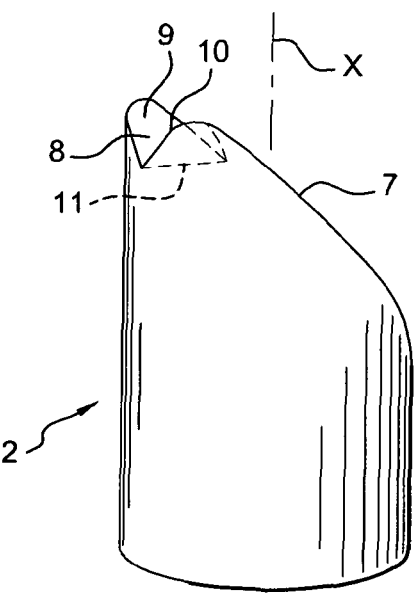
FIG. 5 illustrates a fifth embodiment of an applicator suitable for use in the kits of the present disclosure.

For example, this free end 7 may be defined in a plane perpendicular to the longitudinal axis X, as shown in FIGS. 2 and 4, or else in an oblique plane, different from perpendicular, with this axis X, as represented in FIGS. 1 and 5. In another alternative embodiment, this free end 7 may not be flat and may exhibit at least one concavity or convexity. For example, in FIG. 3, the free end 7 forms a dome overall; it is then convex towards the outside.

The advantage of a portion which is concave towards the outside is that it may make it possible to retain an amount of product therein, for example, when such a concavity is dipped in the product in the foam form. To this end, in the embodiments of FIGS. 2 to 5, the applicator nozzle 2 may comprise a notch 8 (also known as indentation), concave towards the outside, defined through its free end 7. In one embodiment, the applicator nozzle 2 may comprise at least one notch such as that depicted by element 8.

According to another embodiment, the applicator may comprise an application nozzle, one free end of which may exhibit at least one concavity in the form, for example, of an indentation.

Figure 6:
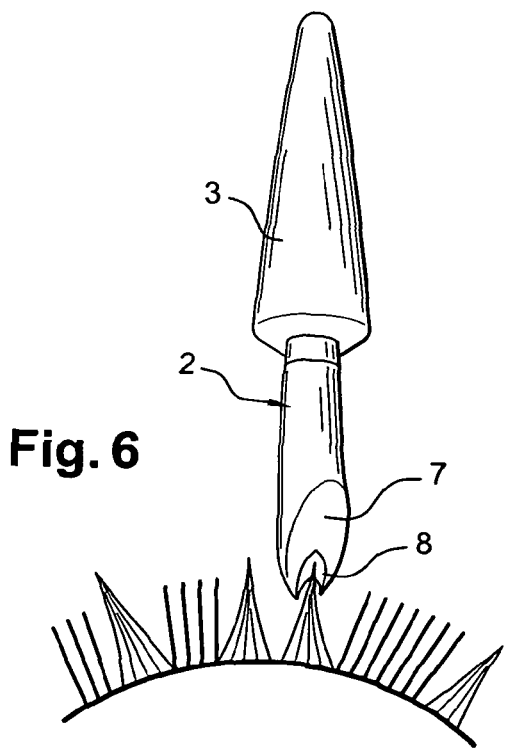
FIG. 6 illustrates the coating of eyelashes causing them to cluster together to form a crest using an applicator according to present disclosure.

Another advantage of the notch 8 is due to the fact that it may be configured to receive a portion of a fringe of eyelashes and that it may make it possible to coat and to arrange the eyelashes of this portion so that they meet at their free ends. This is because eyelashes placed in this notch 8, as represented in FIG. 6, may be coated such that the translational movement of the free end 7 on contact with them causes them to cluster together to from a crest. Making up may be carried out by beginning via the base of the eyelashes and by carrying out a simultaneous translational movement towards the tip of the eyelashes and towards the bottom of the notch 8.

According to a view in cross section perpendicular to the free end 7, this notch 8 may be triangular in cross section, such that the base of this triangle may be chosen according to the width of the portion of eyelashes which it is desired to make up and to arrange in the form of a crest. The height of this triangle may be configured in order to make it possible to drive the eyelashes into this notch 8 over at least 50% of this height, so as to obtain the crests.

According to the embodiments represented in the Figures, the notch 8 may exhibit a triangular cross section according to a cross sectional plane P parallel to the axis X chosen so as to intersect the two side edges 9 and 10 of the notch 8. In at least one embodiment, the bottom of the notch 8 may form a ridge 11 which is linear. In FIGS. 2 to 5, this ridge 11 is a straight line. In an alternative embodiment, this ridge 11 may be curved so as to vary the depth of the notch 8 relative to the application surface defined by the free end 7.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below. Unless otherwise indicated, the amounts are given as percentage by weight.

EXAMPLES

Examples 1 to 3

The following mascaras according to the present disclosure were prepared:

| | Example 1 (%) | Example 2 (%) | Example 3 (%) |
|---|---|---|---|
| Beeswax | 22.5 | 32.2 | 28.5 |
| Sugar stearate | 4.5 | 5.35 | 4.75 |
| PEG-40 monostearate (Myrj 52P ® from ICI Uniquema) | 1.75 | 2.08 | 1.85 |
| Sorbitan tristearate (Span 65V from Uniquema) | 0.77 | 0.9 | 0.8 |
| Apricot kernel oil | 4.5 | — | — |
| Carbon black | 2.7 | — | — |
| Black iron oxide | — | 8 | 7.1 |
| Sodium laureth sulphate | 4.5 | 4.8 | 4.75 |
| Crosslinked poly(acrylic acid)/$C_{10}$–$C_{30}$ alkyl acrylate copolymer (Pemulen TR-2 from Noveon) | 0.27 | 0.29 | — |
| Xanthan gum | — | 0.11 | — |
| Locust bean flour | — | 0.15 | — |
| Alginate | — | — | 0.49 |
| $CaCl_2$ | — | — | 0.1 |
| Preservatives | q.s. | q.s. | q.s. |
| Water | q.s. for 100 | q.s. for 100 | q.s. for 100 |

Procedure

The emulsion was prepared with a Moritz mixer: the compounds of the fatty phase were heated to a temperature of approximately 90° C. The aqueous phase was subsequently poured onto the fatty phase while stirring with a Moritz mixer. Stirring was maintained for 10 minutes while heating.

The emulsion was subsequently poured into a Kenwood beater. When the temperature of the emulsion reached approximately 60° C. during the cooling, it was expanded in volume for 5 minutes.

The density, rigidity modulus, and solids content parameters were measured for each of the compositions according to the protocols described above.

The results are presented in the following table:

|  | Density | Gp (Pa) | Solids content (%) |
|---|---|---|---|
| Example 1 | 0.35 | 350 | 41.6 |
| Example 2 | 0.5 | 1600 | 55.4 |
| Example 3 | 0.66 | 23 600 | 49.5 |

Example 4

The following mascara according to the present disclosure was prepared:

|  | Example 4 |
|---|---|
| Carnauba wax | 25 |
| Sugar stearate | 5 |
| PEG-40 monostearate (Myrj 52P ® from ICI Uniquema) | 1.95 |
| Sorbitan tristearate (Span 65V from Uniquema) | 0.85 |
| Apricot kernel oil | 5 |
| Black iron oxide | 3 |
| Sodium laureth sulphate | 5 |
| Crosslinked poly(acrylic acid)/ $C_{10}$–$C_{30}$ alkyl acrylate copolymer (Pemulen TR-2 from Noveon) | 0.3 |
| Preservatives | q.s. |
| Water | q.s. for 100% |

Procedure:

The compounds of the fatty phase were heated to a temperature of approximately 90° C. The aqueous phase was subsequently poured onto the fatty phase while stirring using a Moritz mixer. Stirring was maintained for 10 minutes while heating.

The emulsion was subsequently poured into a Kenwood beater. When the temperature of the emulsion reached approximately 80° C. during the cooling, it was expanded in volume for 2 minutes.

The density, rigidity modulus, and solids content parameters of the composition were measured according to the protocols described above. The results are presented in the table below:

|  | Density | Gp (Pa) | Solids content (%) |
|---|---|---|---|
| Example 4 | 0.73 | 25 000 | 45.9 |

What is claimed is:

1. A process for coating eyelashes, comprising applying to eyelashes at least one layer of at least one composition in the form of a foam, wherein the at least one composition is a non-delayed expansion composition comprising air bubbles having a number average diameter of less than or equal to 1 mm, and has a density of less than or equal to 0.95 g/cm$^3$ and comprises:
   a dry matter present in an amount ranging from 35% to 50% by weight, with respect to the total weight of the at least one composition,
   at least one wax,
   an emulsifying system comprising at least one anionic surfactant,
   at least one liquid fatty phase, wherein the liquid fatty phase is a non-volatile oil, and
   at least one liquid-fatty-phase structuring agent chosen from pasty fatty substances, semicrystalline polymers, lipophilic gelling agents, and mixtures thereof.

2. A process for coating eyelashes, comprising applying to eyelashes at least one layer of at least one composition in the form of a foam, wherein the at least one composition is a non-delayed expansion composition comprising air bubbles having a number average diameter of less than or equal to 1 mm, and has a density of less than or equal to 0.95 g/cm$^3$ and comprises:
   a dry matter present in an amount ranging from 35% to 50% by weight, with respect to the total weight of the at least one composition,
   at least one wax,
   an emulsifying system comprising at least one anionic surfactant,
   at least one aqueous phase,
   at least one hydrophilic gelling agent,
   at least one liquid fatty phase wherein the liquid fatty phase is a non-volatile oil, and
   at least one liquid-fatty-phase structuring agent chosen from pasty fatty substances, semi crystalline polymers, lipophilic gelling agents, and mixtures thereof.

3. The process according to claim 1, wherein the at least one liquid fatty phase is present in the composition in an amount ranging from 0.1% to 30% by weight, with respect to the total weight of the composition.

4. The process according to claim 3, wherein the at least one liquid fatty phase is present in the composition in an amount ranging from 1% to 20% by weight, with respect to the total weight of the composition.

5. The process according to claim 1, wherein the at least one structuring agent is present in the composition in an amount ranging from 0.1 to 60% by weight, with respect to the total weight of the composition.

6. The process according to claim 5, wherein the at least one structuring agent is present in the composition in an amount ranging from 1 to 40% by weight, with respect to the total weight of the composition.

7. The process according to claim 1, wherein the composition comprises at least one aqueous phase.

8. The process according to claim 2, wherein the at least one aqueous phase is present in the composition in an amount ranging from 1% to 95% by weight, with respect to the total weight of the composition.

9. The process according to claim 8, wherein the at least one aqueous phase is present in the composition in an amount ranging from 5% to 60% by weight, with respect to the total weight of the composition.

10. The process according to claim 1, wherein the composition comprises at least one hydrophilic gelling agent.

11. The process according to claim 2, wherein the at least one hydrophilic gelling agent is from the group consisting of
- a homo- or copolymer of acrylic acid and methacrylic acid and a salt or ester therof,
- a copolymer of acrylic acid and of acrylamide in the form of a sodium salt,
- a sodium salt of poly(hydroxycarboxylic acid),
- a poly(acrylic acid)/alkyl acrylate s copolymer,
- AMPS (poly(acrylamidomethylpropanesulphonic acid) partially neutralized with aqueous ammonia and highly crosslinked),
- AMPS/acrylamide copolymer,
- a copolymer of AMPS and of an alkyl methacrylate which is polyoxyethylenated (crosslinked or noncrosslinked),
- a plant protein,
- an animal protein;
- a cellulose polymer and a quaternized cellulose derivative;
- an acrylic polymer and copolymer;
- a vinyl polymer;
- an optionally modified polymer of natural origin; and
- mixtures thereof.

12. The process according to claim 11, wherein the at least one hydrophilic gelling agent is a vinyl polymer selected from the group consisting of a polyvinylpyrrolidone, a copolymer of methyl vinyl ether and of malic anhydride, a copolymer of vinyl acetate and of crotonic acid, a copolymer of vinylpyrrolidone and of vinyl acetate, a copolymer of vinylpyrrolidone and of caprolactam, and poly(vinyl alcohol).

13. The process according to claim 11, wherein the at least one hydrophilic gelling agent is an optionally modified polymer of natural origin is selected from the group consisting of:
- gums arabic, guar gum, xanthan derivatives, karaya gum or locust bean gum; Alginates, and carrageenans;
- glycoaminoglycans, hyaluronic acid and its derivatives;
- shellac resin, gum sandarac, dammars, elemis, and copals;
- deoxyribonucleic acid; and
- mucopolysaccharides.

14. The process according to claim 2, wherein the at least one hydrophilic gelling agent is present in the composition in a dry matter content ranging from 0.01% to 30% by weight, with respect to the total weight of the composition.

15. The process according to claim 14, wherein the at least one hydrophilic gelling agent is present in a dry matter content ranging from 0.1% to 10% by weight, with respect to the total weight of the composition.

16. The process according to claim 1, wherein the composition comprises at least one coloring material.

17. The process according to claim 2, wherein the composition comprises at least one coloring material.

* * * * *